(12) United States Patent
Chen et al.

(10) Patent No.: US 8,273,388 B2
(45) Date of Patent: Sep. 25, 2012

(54) **EXTRACT OF *POLYGONUM MULTIFLORUM* THUNB. EX MURRAY VAR. *HYPOLEUCUM* AND COMPOSITIONS FOR IMPROVING METABOLIC SYNDROME**

(75) Inventors: Chi-Hua Chen, Hsinchu (TW); Shiow-Wen Chen, Hsinchu (TW); Yuarn-Yee Chang, Hsinchu (TW); Wen-Kia Liu, Hsinchu (TW)

(73) Assignee: Food Industry Research & Development Institute, Hsinchu (TW)

( * ) Notice: Subject to any disclaimer, the term of this patent is extended or adjusted under 35 U.S.C. 154(b) by 2 days.

(21) Appl. No.: 13/098,142

(22) Filed: Apr. 29, 2011

(65) Prior Publication Data

US 2011/0206785 A1     Aug. 25, 2011

Related U.S. Application Data

(62) Division of application No. 12/155,743, filed on Jun. 9, 2008, now abandoned.

(30) Foreign Application Priority Data

Aug. 3, 2007   (TW) ............................... 96128525 A
Nov. 27, 2007  (TW) ............................... 96144911 A

(51) Int. Cl.
    *A61K 36/00*     (2006.01)
(52) U.S. Cl. ........................................................ 424/725
(58) Field of Classification Search .................. None
    See application file for complete search history.

(56) References Cited

U.S. PATENT DOCUMENTS

| 5,531,991 A | 7/1996 | Cheng et al. |
| 6,200,569 B1 * | 3/2001 | Cheng ........................... 424/739 |
| 2004/0005288 A1 | 1/2004 | Lin et al. |

FOREIGN PATENT DOCUMENTS

EP     1829519 A1     9/2007

OTHER PUBLICATIONS

Small, G., et al., "A Sensitive Spectrophotometric Assay for Peroxisomal acyl-CoA oxidase", Biochemical Journal, vol. 227, pp. 2005-210, 1985.
Tanabe, T., et al., "Acetyl-CoA Carobxylase from Rat Liver", Methods in Enzymology, vol. 71, pp. 5-16, 1981.

* cited by examiner

*Primary Examiner* — Christopher R. Tate
*Assistant Examiner* — Randall Winston
(74) *Attorney, Agent, or Firm* — Andrews Kurth LLP; Michael Ye

(57) ABSTRACT

An extract of *Polygonum multiflorum* Thunb. ex Murray var. *hypoleucum* (Ohwi) or of *Polygonum hypoleucum* (Ohwi) for improving metabolic syndrome is prepared by the following method: (a) providing fresh or dry *Polygonum multiflorum* Thunb. ex Murray var. *hypoleucum* (Ohwi) or *Polygonum hypoleucum* (Ohwi) in partial or whole plant; (b) extracting the partial or whole plant by a solvent to obtain a crude extract; (c) condensing and drying the crude extract to obtain an extract product; and (d) collecting the extract product. The present invention also relates to a pharmaceutical and a food composition having the above extract for improving the metabolic syndromes. The extract of the present invention can be easily prepared and is demonstrated to modulate the levels of both blood glucose and blood lipid, to inhibit the activities of glycolytic enzymes and acetyl-CoA carboxylase, and to stimulate acyl-CoA oxidase. The extract of the present invention is capable of improving metabolic syndromes.

8 Claims, 3 Drawing Sheets

EXTRACT OF *POLYGONUM MULTIFLORUM* THUNB. EX MURRAY VAR. *HYPOLEUCUM* AND COMPOSITIONS FOR IMPROVING METABOLIC SYNDROME

CROSS REFERENCE

The present invention is a divisional application claiming the benefit of U.S. patent application Ser. No. 12/155,743 filed on Jun. 9, 2008.

BACKGROUND OF THE INVENTION

1. Field of the Invention

The present invention relates to an extract of *Polygonum multiflorum* Thunb. ex Murray var. *hypoleucum* (Ohwi), especially to an extract of *Polygonum multiflorum* Thunb. ex Murray var. *hypoleucum* (Ohwi) for improving metabolic syndrome.

2. Description of the Related Art

Metabolic syndrome is a combination of medical disorders that increase a person's risk of developing cardiovascular diseases and diabetes. Metabolic syndrome affects a large number of people in a clustered fashion. Recently, with changing dietary habits and lifestyle, more and more people are being diagnosed as having metabolic syndrome that have symptoms including high blood glucose, high blood pressure or high blood lipid level.

Metabolic syndrome may specifically refer to insulin resistance syndrome.

*Polygonum multiflorum* Thunb. ex Murray var. *hypoleucum* (Ohwi), or *Polygonum hypoleucum* (Ohwi), is a special, endemic variety found in Taiwan.

Unlike the typical variety of *Polygonum multiflorum*, *Polygonum multiflorum* Thunb. ex Murray var *hypoleucum* (Ohwi) lacks the characteristic enlarged root part and is commonly used in folk medicine for treating cold, coughing or arthritis.

U.S. Pat. No. 5,531,991 teaches a composition and method for treating hyperglycemia, which utilizes an extract of the Chinese herb *Polygonum multiflorum*. The herb is extracted with 0.1 N $NH_4OH$ and centrifuged. A supernatant is applied to a Sephadex G-25 column. Three fractions are collected. One fraction exhibits a high insulin-potentiating activity in fat cell assays and is shown to lower blood glucose levels.

U.S. Pat. No. 6,200,569 teaches a composition and method for increasing insulin activity, which provides a composition comprising an insulin potentiating agent; such composition comprises one or more substances derived from a water extract of *Polygonum multiflorum*, *Agaricaceae* or *Cinnamomum mairei*. The invention also provides a method for treating hyperglycemia in a patient as an insulin-potentiating agent. The method can be used to decrease blood glucose, glycosylated hemoglobin or glucose level.

The foregoing prior arts relate exclusively to use of *Polygonum multiflorum* extract to control glucose level by stimulating the activity of insulin. However, the foregoing prior arts are not capable of use for modulating the blood lipid, nor improving metabolic syndrome.

Moreover, EP 1 829 519 A1 teaches a pharmaceutical composition comprising *Polygonum multiflorum* Thunb. which comprises *Polygonum multiflorum* Thunb. *Fructus Crataegi*, *Salvia miltiorrhiza Bunge* and *Radix Notog inseng*. The composition has an effect of lowering blood lipid and therefore can be used in preparation of drugs for treatment and prevention of hyperlipidemia. The invention also teaches a method to treat and prevent hyperlipidemia. However, the composition must be used as a whole. In addition, the foregoing patent did not disclose how to modulate blood glucose level nor to improve metabolic syndrome.

As disclosed herein, pharmaceutical compositions and food additives merely provide a single effect on decreasing either blood glucose or blood lipid; yet no related prior art has been taught for using *Polygonum multiflorum* Thunb. ex Murray var. *hypoleucum* (Ohwi), or *Polygonum hypoleucum* (Ohwi) for treating metabolic syndrome. Furthermore, the foregoing prior arts use the typical variety of *Polygonum multiflorum*.

The population of patients with metabolic syndrome has been increasing. To discover a compound or composition, especially a natural plant composition having medical effects in preventing insulin resistance and further to improve metabolic syndrome is important in the field.

SUMMARY OF THE INVENTION

The main objective of the present invention is to prepare an extract of *Polygonum multiflorum* Thunb. ex Murray var. *hypoleucum* (Ohwi), or of *Polygonum hypoleucum* (Ohwi) for improving metabolic syndrome.

To achieve the foregoing objective, an extract of *Polygonum multiflorum* Thunb. ex Murray var. *hypoleucum* (Ohwi), or *Polygonum hypoleucum* (Ohwi) for improving metabolic syndrome in accordance with the present invention being prepared by the following method, comprising:

(a) providing fresh or dry *Polygonum multiflorum* Thunb. ex Murray var. *hypoleucum* (Ohwi), or *Polygonum hypoleucum* (Ohwi) in partial or whole plant;

(b) extracting *Polygonum multiflorum* Thunb. ex Murray var. *hypoleucum* (Ohwi), or *Polygonum hypoleucum* (Ohwi) by a solvent to obtain a crude extract;

(c) condensing and drying the crude extract to obtain a *Polygonum multiflorum* Thunb. ex Murray var. *hypoleucum* (Ohwi), or *Polygonum hypoleucum* (Ohwi) extract product; and (d) collecting the *Polygonum multiflorum* Thunb. ex Murray var. *hypoleucum* (Ohwi), or *Polygonum hypoleucum* (Ohwi) extract product.

One preferred embodiment, the fresh or dry *Polygonum multiflorum* Thunb. ex Murray var. *hypoleucum* (Ohwi), or *Polygonum hypoleucum* (Ohwi) in partial is stem or root of *Polygonum multiflorum* Thunb. ex Murray var. *hypoleucum* (Ohwi), or of *Polygonum hypoleucum* (Ohwi).

Another preferred embodiment, the solvent is water, alcohol, aqueous alcohol solution or ethyl acetate.

Preferably, the solvent comprises 25-100 wt % of ethanol and 75-0 wt % of water; more preferably, the solvent comprises 70-100 wt % ethanol and 30-0 wt % of water.

One preferred embodiment, the solvent is an acidic alcohol; preferably, an acidic alcohol containing 0.1% of hydrochloric acid.

Preferably, *Polygonum multiflorum* Thunb. ex Murray var. *hypoleucum* (Ohwi), or *Polygonum hypoleucum* (Ohwi) and the solvent have a weight to volume ratio between 1:5 to 1:20.

One preferred embodiment, the step (b) is proceeded at room temperature.

The present invention also relates to a method for improving metabolic syndrome by administering to a therapeutically effective amount of extract of *Polygonum multiflorum* Thunb. ex Murray var. *hypoleucum* (Ohwi), or of *Polygonum hypoleucum* (Ohwi) to a subject in needed.

One preferred embodiment, the extract of *Polygonum multiflorum* Thunb. ex Murray var. *hypoleucum* (Ohwi), or of *Polygonum hypoleucum* (Ohwi). for improving metabolic syndrome is by inhibiting glucosidic enzymes or acetyl-CoA carboxylase (ACC), stimulating acyl-CoA oxidase (ACO), and modulating the levels of both blood glucose and blood lipid.

Preferably, the metabolic syndrome is insulin resistance syndrome; more preferably, the insulin resistance syndrome is high blood glucose or blood lipid The present invention also relates to an extract of *Polygonum multiflorum* Thunb. ex Murray var. *hypoleucum* (Ohwi), or of *Polygonum hypoleucum* (Ohwi) for improving metabolic syndrome prepared by the following method, comprising:

(a) providing fresh or dry stem and root of *Polygonum multiflorum* Thunb. ex Murray var. *hypoleucum* (Ohwi), or of *Polygonum hypoleucum* (Ohwi);

(b) extracting *Polygonum multiflorum* Thunb. ex Murray var. *hypoleucum* (Ohwi), or *Polygonum hypoleucum* (Ohwi) as a crude extract using an alcohol solvent;

(c) condensing and drying the crude extract as a *Polygonum multiflorum* Thunb. ex Murray var. *hypoleucum* (Ohwi), or *Polygonum hypoleucum* (Ohwi) extract product; and (d) collecting the extract product of *Polygonum multiflorum* Thunb. ex Murray var. *hypoleucum* (Ohwi), or of *Polygonum hypoleucum* (Ohwi).

One preferred embodiment, the solvent comprises 25-100 wt % of ethanol and 75-0 wt % of water; preferably, the solvent comprises 70-100 wt % ethanol and 30-0 wt % of water.

Another preferred embodiment, the solvent is an acidic alcohol.

Preferably, the solvent contains 0.1% of hydrochloric acid.

One preferred embodiment, the *Polygonum multiflorum* Thunb. ex Murray var. *hypoleucum* (Ohwi), or *Polygonum hypoleucum* (Ohwi) and the solvent have a weight to volume ratio between 1:5 to 1:20.

Another preferred embodiment, the step (b) is proceeded at room temperature.

The present invention also relates to a pharmaceutical composition comprising the extract of *Polygonum multiflorum* Thunb. ex Murray var. *hypoleucum* (Ohwi), or of *Polygonum hypoleucum* (Ohwi) obtained from the present invention and at least one pharmaceutically acceptable carrier or excipient.

One preferred embodiment, the pharmaceutically composition is formed as tablet, powder, suspension, chyle fluid, capsule, particle, pill, fluid, alcohol solution or medical syrup.

The present invention also relates to a food composition comprising the extract of *Polygonum multiflorum* Thunb. ex Murray var. *hypoleucum* (Ohwi), or of *Polygonum hypoleucum* (Ohwi) obtained from the present invention.

The extract of *Polygonum multiflorum* Thunb. ex Murray var. *hypoleucum* (Ohwi), or of *Polygonum hypoleucum* (Ohwi) of the present invention is prepared easily and can modulate blood glucose and blood lipid levels by inhibiting the activities of glucosidic enzymes, or acetyl-CoA carboxylase, stimulating acyl-CoA oxidase activities. Other objectives, advantages and novel features of the invention will become more apparent from the following detailed description when taken in conjunction with the accompanying drawings.

DETAILED DESCRIPTION OF THE PREFERRED EMBODIMENTS

*Polygonum multiflorum* Thunb. ex Murray var. *hypoleucum* (Ohwi) Liu, Ying & Lai, common name Taiwan tuber fleeceflower, is also known as *Polygonum hypoleucum* (Ohwi), or *Pleuropterus hypoleucus* (Nakai). The enlarged root tuber of *Polygonum multiflorum* is one of the most famous tonic medicine in China and Japan. As an endemic variety of *Polygonum multiflorum*, *Polygonum multiflorum* Thunb. ex Murray var. *hypoleucum* (Ohwi) lacks the characteristic feature of enlarged root tuber, is often found from low to medium altitudes of Taiwan. The whole plant are used in folk medicine for treating cold, coughing and arthritis, the leaves for topical application of treating cuts, too.

The fresh or dry *Polygonum multiflorum* Thunb. ex Murray var. *hypoleucum* (Ohwi) in partial or whole plant as defined herein is the leaves, stems, or roots of *Polygonum multiflorum* Thunb. ex Murray var. *hypoleucum* (Ohwi).

The solvent as defined herein is a polar solvent and may be water, alcohol, aqueous alcohol solution or ethyl acetate.

Metabolic syndrome as defined herein may specifically refer to insulin resistance syndrome, which may have symptoms including high blood glucose, dyslipidemia, and high blood pressure.

The pharmaceutically acceptable carrier or pharmaceutical carrier as defined herein refers to materials suitable for pharmaceutical administration. They are inert agents or vehicles for delivering one or more active agents to a subject.

The excipient is substantially non-toxic and allows a medical composition to remain stable and bio-available.

The extract of *Polygonum multiflorum* Thunb. ex Murray var. *hypoleucum* (Ohwi), or of *Polygonum hypoleucum* (Ohwi), as defined herein are those active ingredients of the *Polygonum multiflorum* Thunb. ex Murray var. *hypoleucum* (Ohwi), or of *Polygonum hypoleucum* (Ohwi), which can be used to modulate the concentrations of blood glucose and blood lipid by interacting with enzymes including intestinal glucosidic and hepatic enzymes. More specifically, *Polygonum multiflorum* Thunb. ex Murray var. *hypoleucum* (Ohwi), or *Polygonum hypoleucum* (Ohwi) exhibits biochemical efficacies with regards to inhibiting both alpha-glucosidase and ACC and stimulating ACO. More specifically, the extract of *Polygonum multiflorum* Thunb. ex Murray var. *hypoleucum* (Ohwi), or of *Polygonum hypoleucum* (Ohwi) can be implemented in a pharmaceutical composition or food composition for improving metabolic syndrome.

The term "a subject in needed" as used herein is any patient suffering from metabolic syndrome. The term "subject" is known in the art, and, as used herein, refers to a warm-blooded animal, more preferably a mammal, including, e.g., non-human animals such as rats, mice, cats, dogs, sheep, horses, cattle, in addition to humans. In a preferred embodiment, the subject is a human.

Figure 1:
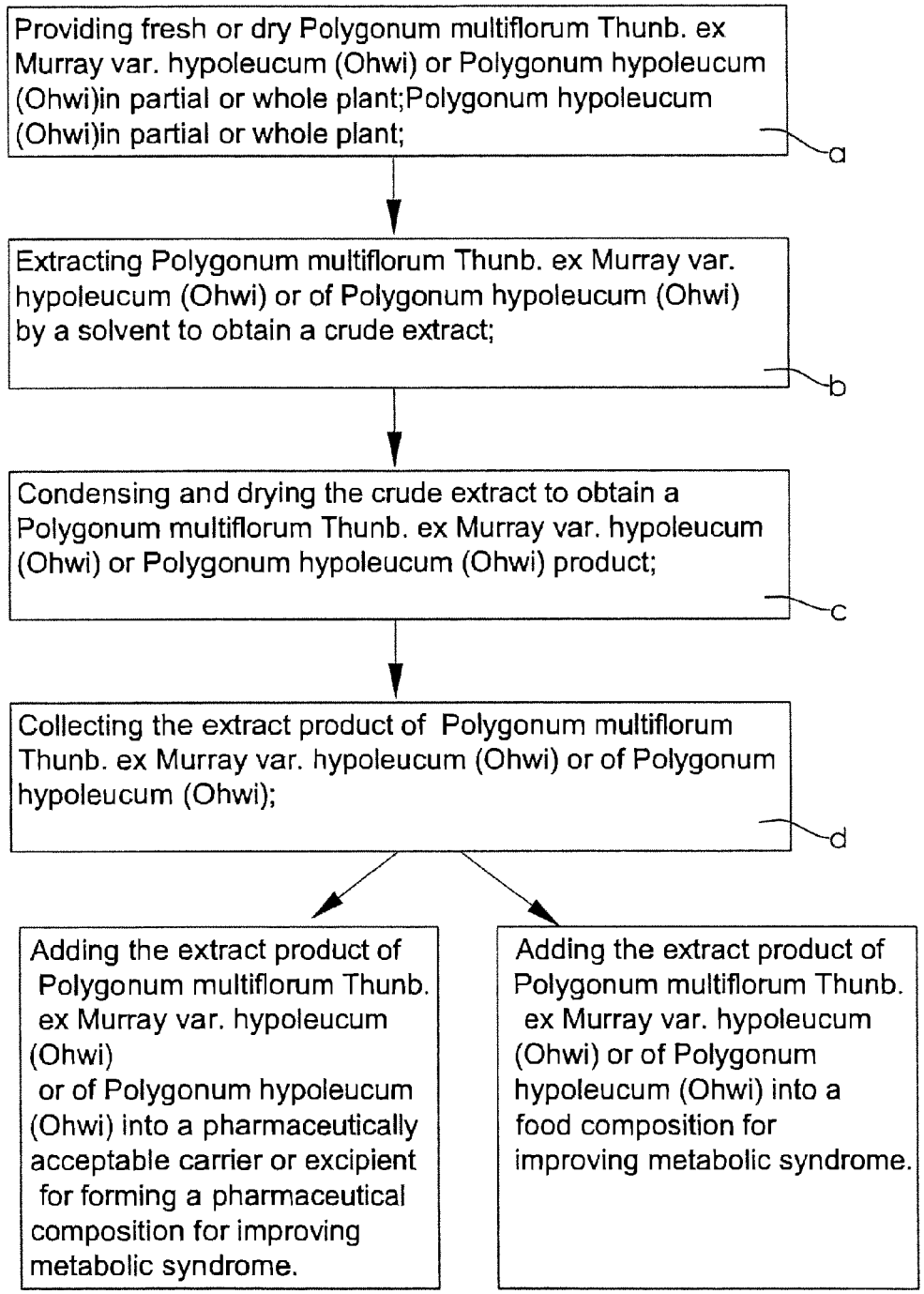
FIG. 1 is a flow chart describing a method for preparing the extract of *Polygonum multiflorum* Thunb. ex Murray var. *hypoleucum* (Ohwi), or of *Polygonum hypoleucum* (Ohwi) in accordance with the present invention.

With reference to FIG. 1, the extract of *Polygonum multiflorum* Thunb. ex Murray var. *hypoleucum* (Ohwi), or of *Polygonum hypoleucum* (Ohwi) for improving metabolic syndrome in accordance with the present invention is prepared by a method comprising steps of: (a) providing fresh or dry *Polygonum multiflorum* Thunb. ex Murray var. *hypoleucum* (Ohwi) or *Polygonum hypoleucum* (Ohwi) in partial or whole plant; (b) extracting *Polygonum multiflorum* Thunb. ex Murray var. *hypoleucum* (Ohwi) or *Polygonum hypoleucum* (Ohwi) by a solvent to obtain a crude extract; (c) condensing and drying the crude extract to obtain a *Polygonum multiflorum* Thunb. ex Murray var. *hypoleucum* (Ohwi) or *Polygonum hypoleucum* (Ohwi) extract product; (d) collecting the extract product of *Polygonum multiflorum* Thunb. ex Murray var. *hypoleucum* (Ohwi), or of *Polygonum hypoleucum* (Ohwi). The extract product of *Polygonum multiflorum* Thunb. ex Murray var. *hypoleucum* (Ohwi) or of *Polygonum hypoleucum* (Ohwi) may further be added into a pharmaceutically acceptable carrier or excipient for forming a pharmaceutical composition for improving metabolic syndrome. The extract product of *Polygonum multiflorum* Thunb. ex Murray var. *hypoleucum* (Ohwi) or of *Polygonum hypoleucum* (Ohwi) may also be added to form a food composition for improving metabolic syndrome.

The condensing and drying methods as defined in the present invention may comprise freezing and drying, depressing and condensing or other condensing and drying methods known in the art.

The pharmaceutical composition according to the present invention may be dosed in oral administration, and the form of dosage can be a pill, tablet, powder, suspension, chyle fluid, capsule, particle, fluid, a solution including alcohol and aqueous, or medical syrup.

Example 1

Preparation of Extracts of *Polygonum multiflorum* Thunb. ex Murray var. *hypoleucum* (Ohwi) or of *Polygonum hypoleucum* (Ohwi)

i) Acidic Alcohol Extract

*Polygonum multiflorum* Thunb. ex Murray var. *hypoleucum* (Ohwi) or *Polygonum hypoleucum* (Ohwi) was machine-grounded, then extracted with an acidic alcohol containing 0.1% HCl. The weight to volume ratio of grounded *Polygonum multiflorum* Thunb. ex Murray var. *hypoleucum* (Ohwi) or *Polygonum hypoleucum* (Ohwi) and acidic alcohol was about 1:8. The mix was left at room temperature with or without shaking for 72 hours, filtered through 2 layers of cheesecloth and centrifuged at 6,000 rpm for 15 min. The solution was collected and concentrated. The extraction rate is about 6.9%.

A 50 mg/ml stock solution was prepared with water.

ii) Hot Water Extract:

*Polygonum multiflorum* Thunb. ex Murray var. *hypoleucum* (Ohwi) or *Polygonum hypoleucum* (Ohwi) was heated in water for 2 hours. The weight to volume ratio of *Polygonum multiflorum* Thunb. ex Murray var. *hypoleucum* (Ohwi) or *Polygonum hypoleucum* (Ohwi) and water was about 1:20. The extract was filtered through 2 layers of cheesecloth and freeze-dried. The extraction rate is about 9.2%. A 50 mg/ml stock solution was prepared with water.

Example 2

The Inhibitory Effects of Extracts of *Polygonum multiflorum* Thunb. ex Murray var. *hypoleucum* (Ohwi) or of *Polygonum hypoleucum* (Ohwi) on α-Glucosidase Extract #1 and #2 are different batches of acidic alcohol extracts, and extract #3 is hot water extract, prepared as described in example 1.

The inhibitory effects of the 3 extracts on α-glucosidase was assayed as following:

1. Both enzyme α-glucosidase (EC 3.2.1.20, G5003, Sigma-Aldrich Co., USA) and substrate p-nitrophenyl α-D-glucopyranoside (pNP-G) (Sigma-Aldrich Co., USA) solutions were prepared with 100 mM, pH 7 M phosphoric acid buffer solution to reached a concentration of 1 U/ml and $5 \times 10^{-3}$ M, respectively.

2. 40 μl of 0.4 M, pH 7.0 phosphoric acid buffer, 10 μl of α-glucosidase, 50 μl of serial dilutions of the extracts of *Polygonum multiflorum* Thunb. ex Murray var. *hypoleucum* (Ohwi) or of *Polygonum hypoleucum* (Ohwi) and 170 of deionized water were added orderly into each well of a 96-well plate 3. An aliquot of 30 μl preheated substrate solution was added into each well, mixed thoroughly and incubated at 37° C. for 10 minutes.

4. Absorbance at 405 nm wavelength (Power Wave XS, Bio Tek Co., USA) was recorded before and after incubation. $IC_{50}$ represents the concentration needed to inhibit 50% of the activity of α-glucosidase. Table 1 shows the results of $IC_{50}$ for extracts #1-3.

TABLE 1

| | $IC_{50}$ for extracts #1-3 | | |
| --- | --- | --- | --- |
| | extract #1 | extract #2 | extract #3 |
| $IC_{50}$ (μg/ml) | 5.5 ± 0.5 | 6.5 ± 0.7 | 17.1 ± 0.4 |

Both acidic alcohol extracts and hot water extracts demonstrated inhibitory effects on the activity of α-glucosidase. One preferred embodiment of the present invention is acidic alcohol extract.

Example 3

The inhibitory Effects of Extracts of *Polygonum multiflorum* Thunb. ex Murray var. *hypoleucum* (Ohwi) or of *Polygonum hypoleucum* (Ohwi) on Different Glycosidic Enzymes Rat intestinal acetone powder (Sigma Chemical Co., St. Louis, Mo.) was provided as a source of glycosidic enzyme to test the inhibitory effects of the acidic alcohol extracts with various glycosidic substrates (maltose, starch and sucrose) (Table 2).

TABLE 2

Values of $IC_{50}$ of the acidic alcohol extract of *Polygonum multiflorum* Thunb. ex Murray var. *hypoleucum* (Ohwi) for various glycosidic enzymes

| | $IC_{50}$ (mg/ml) | | |
| --- | --- | --- | --- |
| | Maltase | α-amylase | Sucrase |
| Acidic alcohol extract | 0.6 | 1.9 | 3.1 |

As shown in Table 2, the acidic alcohol extract was capable of inhibiting the activities of maltase, α-amylase and sucrase, with the strongest effects on maltase.

Example 4

Preparation of Lipid-Soluble Extracts of *Polygonum multiflorum* Thunb. ex Murray var. *hypoleucum* (Ohwi) or of *Polygonum hypoleucum* (Ohwi)

*Polygonum multiflorum* Thunb. ex Murray var. *hypoleucum* (Ohwi) or *Polygonum hypoleucum* (Ohwi) was machine-grounded, 50 wt % of methanol was added at a weight to volume ratio about 1:10. The mix was kept at room temperature with shaking for 24 hours, and filtered. An equal volume of water:ethyl acetate (1:1, vol:vol) was added to the filtrate for liquid-liquid extraction. The upper layer was obtained. An equal volume of 5 wt % of sodium bicarbonate-($NaHCO_3$) was added to remove free fatty acids. The ethyl acetate layer was collected, condensed and dried. An extraction rate was about 0.91%.

The obtained lipid-soluble extract was dissolved in dimethyl sulfoxide (DMSO) at a concentration of 10 mg/ml.

Example 5

Inhibitory Effects of Extracts of *Polygonum multiflorum* Thunb. ex Murray var. *hypoleucum* (Ohwi) or of *Polygonum hypoleucum* (Ohwi) on Acetyl-CoA Carboxylase (ACC)

Acetyl-CoA carboxykase (ACC) is one of the key enzymes involved in fatty acid synthesis. The product of ACC reaction, malonyl-CoA, is both a substrate of fatty acid synthase (FAS) and an inhibitor of carnitin palmitoyl CoA-transferase (CPT). Therefore, inhibition of ACC not only reduce the synthesis of endogenous lipid, but also increase the oxidation of mitochondrial fatty acid.

ACC was isolated and purified from rat liver, and assayed as previously described (Tanabe T., Nakanishi, S., Hashimoto T., Ogiwara, H., Nikawa J., Numa S. 1981. Acetyl-CoA carboxylase from rat liver, Meth. Enzymol. 71 (pt C): 5-16).

TABLE 3

Inhibitory effects of extracts of *Polygonum multiflorum* Thunb. ex Murray var. *hypoleucum* (Ohwi) or of *Polygonum hypoleucum* (Ohwi) on ACC

|  | ACC inhibition (%) |
| --- | --- |
| Acidic alcohol extracts (0.05 mg/ml) | 61.27 ± 5.4 |
| Lipid-soluble extracts (0.05 mg/ml) | 45.99 ± 11.9 |

As demonstrated in Table 3, both acidic alcohol extract and lipid-soluble extract of *Polygonum multiflorum* Thunb. ex Murray var. *hypoleucum* (Ohwi) or of *Polygonum hypoleucum* (Ohwi) exhibited inhibitory effects on ACC.

Figure 2:
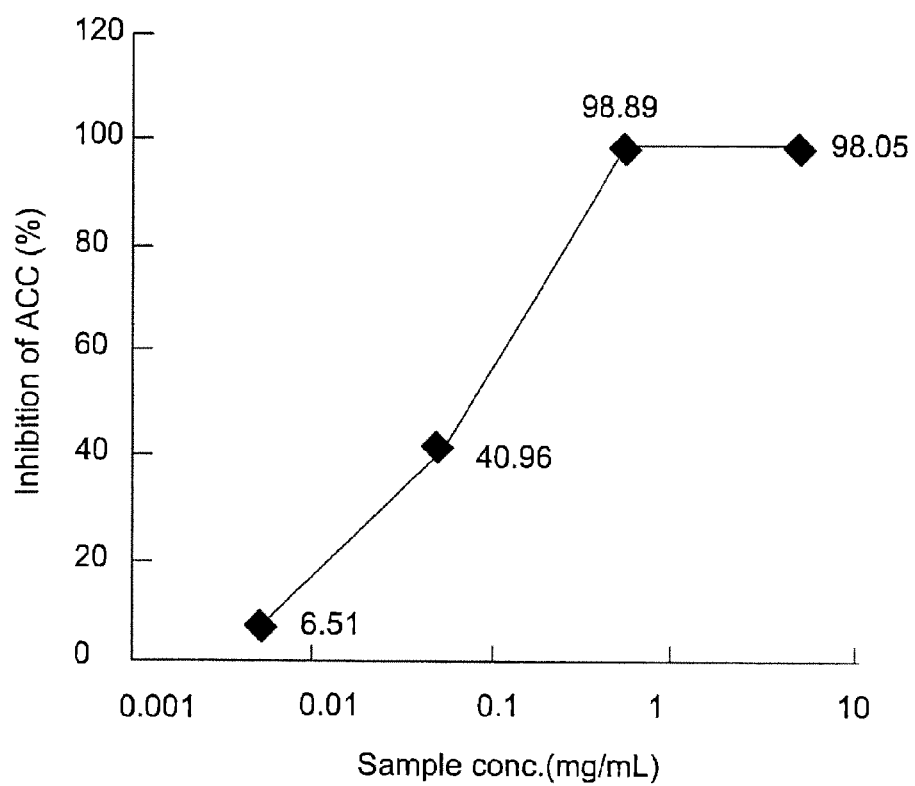
FIG. 2 is a plot showing the inhibitory effects of the extract of *Polygonum multiflorum* Thunb. ex Murray var. *hypoleucum* (Ohwi), or of *Polygonum hypoleucum* (Ohwi) on acetyl-CoA carboxylase (ACC) activity.

FIG. 2 shows the inhibitory effects of different concentrations of acidic alcohol extracts on ACC. The $IC_{50}$ was 0.04 mg/ml.

Example 6

The Stimulatory Effects of the Acidic Alcohol Extract of *Polygonum multiflorum* Thunb. ex Murray var. *hypoleucum* (Ohwi) or of *Polygonum hypoleucum* (Ohwi) on Acyl-CoA Oxidase (ACO)

ACO is one of the key enzymes associated with 3 oxidation of fatty acid. It is also a downstream gene of PPARα, and can be used as a marker of fatty acid oxidation.

Suitable number of hepatic cells H4IIEC3 were seeded in a 12-well plate. Once the cells reached confluence, the media were replaced with either clofibrate or 100 μl/ml of the acidic alcohol extract of *Polygonum multiflorum* Thunb. ex Murray var. *hypoleucum* (Ohwi) or of *Polygonum hypoleucum* (Ohwi). The foregoing mixture solution was incubated for a proper period of time. Then the culture solution was removed, and the cells were collected for ACO analysis.

Figure 3A:
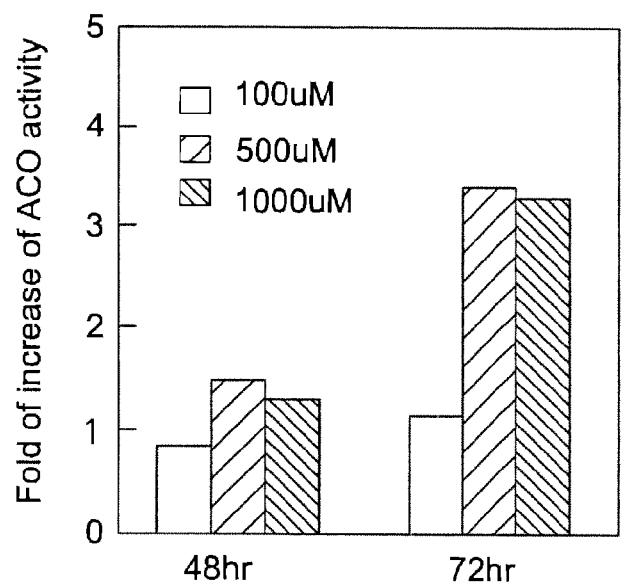
FIG. 3 shows the stimulatory effects of (A) clofibrate and (B) 100 µg/ml of the extract of *Polygonum multiflorum* Thunb. ex Murray var. *hypoleucum* (Ohwi), or of *Polygonum hypoleucum* (Ohwi) on acyl-CoA oxidase (ACO) activity.
Figure 3B:
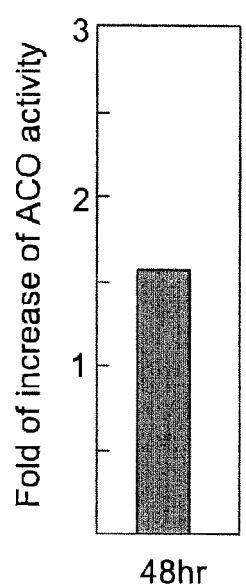

The method of analyzing ACO is described by Small et al. (Small, G M., Burdett, K., and ConNock, M. J. 1985. A sensitive spectrophotometric assay for peroxisomal acyl-CoA oxidase. Biochemical Journal. 227: 205-210). FIG. 3a shows the concentration-dependent stimulatory effects of clofibrate on ACO activity for different time periods (48 and 72 hours). The folds of increases of ACO activities by the acidic alcohol extract of *Polygonum multiflorum* Thunb. ex Murray var. *hypoleucum* (Ohwi) or of *Polygonum hypoleucum* (Ohwi) is shown in FIG. 3b.

Example 7

The Effects of the Acidic Alcohol Extract of *Polygonum multiflorum* Thunb. ex Murray var. *hypoleucum* (Ohwi) or of *Polygonum hypoleucum* (Ohwi) on C57BL/6J Mice Fed on High Fat Diet C57BL/6J mice were fed with a high fat diet comprising 30% (g/g) butter for 8 weeks to induce obese, hypertriglyceridemic and hyperinsulinemic symptoms. The mice with the aforementioned symptoms were divided into 2 groups. One group of the mice was given 1500 mg/kg body weight of the acidic alcohol extract of *Polygonum multiflorum* Thunb. ex Murray var. *hypoleucum* (Ohwi) or of *Polygonum hypoleucum* (Ohwi) (HF+No. 11). The other group, the control group (HF), was given the same volume of water. Both groups were maintained on the same high fat diet. Another group of mice fed on normal chow (LF) was also examined. Oral glucose tolerance test (OGTT) was carried out after 5-week feeding (Table 4). The mice were then sacrificed, and blood and tissues collected for analyses (Table 5).

TABLE 4

Results of oral glucose tolerance test (OGTT) after five-week feeding

|  | Time (min) | LF (n = 14) | HF (n = 6-7) | HF + No. 11 (n = 6-7) |
| --- | --- | --- | --- | --- |
| Concentration of blood glucose (mmol/L) | 0 | $6.1 ± 1.32^a$ | $8.76 ± 2.78^b$ | $7.6 ± 1.27^a$ |
|  | 30 | $10.37 ± 1.45^a$ | $12.27 ± 2.65^b$ | $10.99 ± 1.45^b$ |
|  | 60 | $9.97 ± 1.25^a$ | $12.16 ± 2.16^c$ | $10.63 ± 1.42^b$ |
|  | 90 | $8.75 ± 1.52^a$ | $12.25 ± 3.34^b$ | $10.47 ± 1.65^b$ |
|  | 120 | $8.56 ± 1.55^a$ | $13.74 ± 3.01^c$ | $10.01 ± 1.42^b$ |
| $AUC_{120\,min}$ (mmol*min/L) |  | $656.3 ± 93.3^a$ | $961.2 ± 76.3^c$ | $831.1 ± 76.3^b$ |

Data are expressed as average±standard deviation. Values not sharing the same superscript letters in the same row are significantly different (P<0.05).

Five-week supplementing with the acidic alcohol extract of *Polygonum multiflorum* Thunb. ex Murray var. *hypoleucum* (Ohwi) or of *Polygonum hypoleucum* (Ohwi) significantly decreased the fasting blood glucose level (0 min) of C57BL/6J mice fed on high fat diet Both the blood glucose levels (at 90 and 120 min) and the area under curve of 120 min of (HF+No. 11) group were significantly lower than those of HF group. These results indicate that the acidic alcohol extract of *Polygonum multiflorum* Thunb. ex Murray var. *hypoleucum*

(Ohwi) or of *Polygonum hypoleucum* (Ohwi) not only decreases fasting blood glucose but also improve glucose intolerance.

Table 5 shows that the acidic alcohol extract of Polygonum multiflorum Thunb. ex Murray var. *hypoleucum* (Ohwi) or of *Polygonum hypohucum* (Ohwi) decreases body weight, scrum levels of total cholesterol (TC). triglyceride (TG), insulin and leptin of C57BL/6J mice fed on high fat diets.

|  | LF (n = 14) | HF (n = 6-7) | HF + No. 11 (n = 6-7) |
|---|---|---|---|
| Final body weight (g) | $26.2 \pm 1.2^c$ | $37.0 \pm 1.8^a$ | $35.1 \pm 3.2^b$ |
| Serum TG (mol/ml) | $0.99 \pm 0.23^b$ | $1.38 \pm 0.18^a$ | $1.14 \pm 0.32^b$ |
| Serum TC (mmol/l) | $2.62 \pm 0.43^c$ | $4.68 \pm 0.21^a$ | $3.69 \pm 1.08^b$ |
| Serum insulin (ng/ml) | $0.39 \pm 0.11^b$ | $0.599 \pm 0.2^a$ | $0.462 \pm 0.2^b$ |
| NEFA (mmol/l) | $1.27 \pm 0.16^a$ | $1.63 \pm 0.45^a$ | $1.28 \pm 0.25^a$ |
| Leptin (ng/ml) | $467 \pm 1557^c$ | $5911 \pm 1623^a$ | $4204 \pm 2209^b$ |

Data are expressed as average±standard deviation. Values not sharing the same superscript letters in the same row are significantly different (p<0.05).

The extract of *Polygonum multiflorum* Thunb. ex Murray var. *hypoleucum* (Ohwi) or of *Polygonum hypoleucum* (Ohwi) of the present invention comprises a simple preparing method without special solvents nor complicated procedures.

Moreover, examples above show that the extract of *Polygonum multiflorum* Thunb. ex Murray var. *hypoleucum* (Ohwi) or of *Polygonum hypoleucum* (Ohwi) is able to modulate the concentrations of blood glucose and lipid; inhibit the activities of both glucosidic enzymes and ACC, and increase ACO activities. Therefore, the extract of *Polygonum multiflorum* Thunb. ex Murray var. *hypoleucum* (Ohwi) or of *Polygonum hypoleucum* (Ohwi) is able to improve metabolic syndromes as described.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method for improving metabolic syndrome by administering a therapeutically effective amount of an extract product of *Polygonum multiflorum* Thunb. ex Murray var. *hypoleucum* (Ohwi) or of *Polygonum hypoleucum* (Ohwi) to a subject in need thereof wherein the extract product of *Polygonum multiflorum* Thunb. ex Murray var. *hypoleucum* (Ohwi) or of *Polygonum hypoleucum* (Ohwi) is prepared by the following method, comprising the steps of:

(a) providing fresh or dry *Polygonum multiflorum* Thunb. ex Murray var. *hypoleucum* (Ohwi) or *Polygonum hypoleucum* (Ohwi) in partial or whole plant;

(b) extracting *Polygonum multiflorum* Thunb. ex Murray var. *hypoleucum* (Ohwi) or *Polygonum hypoleucum* (Ohwi) by a solvent of water, alcohol, an aqueous alcohol solution or an ethyl acetate to obtain a crude extract;

(c) condensing and drying the crude extract to obtain a *Polygonum multiflorum* Thunb. ex Murray var. *hypoleucum* (Ohwi) or *Polygonum hypoleucum* (Ohwi) extract product; and (d) collecting the extract product of *Polygonum multiflorum* Thunb. ex Murray var. *hypoleucum* (Ohwi) or of *Polygonum hypoleucum* (Ohwi).

2. The method as claimed in claim 1, wherein the fresh or dry *Polygonum multiflorum* Thunb. ex Murray var. *hypoleucum* (Ohwi) or *Polygonum hypoleucum* (Ohwi) in partial is stem or root of *Polygonum multiflorum* Thunb. ex Murray var. *hypoleucum* (Ohwi) or *Polygonum hypoleucum* (Ohwi).

3. The method as claimed in claim 1, wherein the solvent comprises 25-100 wt % of ethanol and 75-0 wt % of water.

4. The method as claimed in claim 1, wherein the solvent comprises 70-100 wt % ethanol and 30-0 wt % of water.

5. The method as claimed in claim 1, wherein the solvent is an acidic alcohol.

6. The method as claimed in claim 1, wherein the acidic alcohol comprises 0.1 of hydrochloric acid.

7. The method as claimed in claim 1, wherein *Polygonum multiflorum* Thunb. ex Murray var. *hypoleucum* (Ohwi) or *Polygonum hypoleucum* (Ohwi) and the solvent have weight to volume ratio between 1:5 and 1:20.

8. The method as claimed in claim 1, wherein the step (b) extracting *Polygonum multiflorum* Thunb. ex Murray var. *hypoleucum* (Ohwi) or *Polygonum hypoleucum* (Ohwi) by a solvent of water, alcohol, an aqueous alcohol solution or an ethyl acetate to obtain a crude extract is performed at room temperature.

\* \* \* \* \*